United States Patent [19]

Sainz et al.

[11] Patent Number: 4,804,519
[45] Date of Patent: Feb. 14, 1989

[54] SAMPLE ANALYSIS APPARATUS

[75] Inventors: Mario A. Sainz, Londonderry, N.H.; Richard C. Anderson, Jr., Boston, Mass.; Richard J. Belmore, East Bridgewater, Mass.; Stanley B. Smith, Jr., Westford, Mass.

[73] Assignee: Thermo Jarrell Ash Corporation, Waltham, Mass.

[21] Appl. No.: 22,769

[22] Filed: Mar. 6, 1987

[51] Int. Cl.$^4$ .......................... G01N 21/73; G01J 3/42
[52] U.S. Cl. ........................ 422/81; 356/316; 356/319; 366/247; 422/54; 422/68; 436/50; 436/52; 436/53; 436/154; 436/56
[58] Field of Search .................. 422/81, 82, 68, 54, 422/98; 436/52, 53, 56, 50; 356/319, 316; 366/244-249

[56] References Cited

U.S. PATENT DOCUMENTS

| | | |
|---|---|---|
| 3,615,227 | 10/1971 | Molndal .......................... 422/82 X |
| 3,816,075 | 6/1974 | Lambert . |
| 3,864,082 | 2/1975 | Kato . |
| 3,994,687 | 11/1976 | Engelbrecht . |
| 4,361,401 | 11/1982 | Smith, Jr. . |
| 4,441,374 | 4/1984 | Suzuki . |
| 4,512,348 | 4/1985 | Uchigaki et al. ................. 422/81 X |
| 4,590,165 | 5/1986 | Gilles . |

FOREIGN PATENT DOCUMENTS 923285  4/1963  United Kingdom .................. 436/53

Primary Examiner—Michael S. Marcus

[57] ABSTRACT

An analysis system includes a sample inlet, a diluent inlet, and a mixing chamber that has an outlet through which a mixture of the sample and diluent is flowed and in which a mechanical mixing member is housed. Positive displacement pumps preferably concurrently flow diluent to the mixing chamber and draw diluted sample to be analyzed from the mixing chamber. Bubble separation apparatus has a first branch connected to a drain and a second branch connected to the analyzer input. In a particular embodiment, the analyzer apparatus includes a nebulizer that controls the flow rate of the bubble-free stream through the second branch, sample excitation apparatus in the form of an induction coupled plasma (ICP) torch for exciting the sample to spectroemissive levels, and means for spectroanalysis of the excited sample at the output of the torch.

28 Claims, 2 Drawing Sheets

SAMPLE ANALYSIS APPARATUS

This invention relates to sample analysis apparatus, and more particularly to sample analysis apparatus particularly adapted for introducing a diluted viscous sample into an instrument, such as a spectrometer, for trace element analysis.

Sample analysis is in widespread use in industrial, clinical and medical environments. Frequently, samples to be analyzed are diluted with an appropriate diluent. Where the sample to be analyzed is a high viscosity liquid such as oil, brines, sludges and the like, such samples are more difficult to aspirate, to dilute, and to clean from the analysis system.

In accordance with one aspect of the invention, there is provided an analysis system that includes a sample inlet, a diluent inlet, a mixing chamber that has an outlet through which a mixture of the sample and diluent is flowed and in which a mechanical mixing member is housed. Positive displacement pumps preferably concurrently flow diluent to the mixing member and draw diluted sample to be analyzed from the mixing chamber. Bubble separation apparatus has a first branch connected to a drain and a second branch connected to the analyzer input. In a particular embodiment, the analyzer apparatus includes a nebulizer and sample excitation apparatus in the form of an induction coupled plasma (ICP) torch for exciting the sample to spectroemissive levels, together with means for spectroanalysis of the excited sample at the output of the torch.

In accordance with another aspect of the invention, successive sample quantities are flowed through the analysis system with alternating spaced cleaning solvent quantities which include a tag element different from the trace elements in the sample to be analyzed, and the analysis apparatus is controlled to detect the tag element and acquire data at a predetermined time after detection of a preestablished tag element characteristic.

In preferred embodiments, the mixing chamber has a volume of less than one milliliter and contains a bladed impeller that is driven in rotation at relatively high speeds (up to over 100 RPM) to provide mixing of sample and diluent drawn into the mixing chamber, together with a positive flow pump in the form of a peristaltic pump that flows the resulting mixture to the debubbler apparatus. The mechanical mixer produces reliable mixing of viscous samples and diluent, and the bubbles produced by sampling artifacts, cavitation and similar effects are drawn along a main flow path through the debubbler apparatus with an intact (bubble-free) stream of diluted sample being flowed to the nebulizer. The debubbler apparatus includes a main upwardly inclined flow branch and a generally vertical analyzer branch through which a minor fraction of the sample mixture is flowed to the nebulizer that controls the flow rate over the analyzer branch, the main flow and branch passages each having a cross-sectional dimension of less than one-half centimeter. The system is particularly useful in dilution of viscous liquid such as heavy (90 weight) motor oils, such viscous liquids being analyzed for trace elements such as wear metals and other elements including calcium, barium, zinc, sodium, magnesium, phosphorous and the like.

In a particular analysis system, the cleaning liquid is hydrocarbon-based and a suitable tag element in the cleaning liquid is cobalt. Induction coupled plasma apparatus excites diluted liquids to spectroemissive levels, and a photosensor responds to the output of the induction coupled plasma apparatus. A control channel and a plurality of data acquisition channels all respond to the output of the photosensor. In response to a decrease (one-half maximum) in the sensed magnitude of a specific wavelength characteristic of the cobalt tag material, the control channel produces an output that activates the data acquisition channels to acquire data on elements in the sample that are excited to spectroemissive levels by the induction coupled plasma apparatus.

Other features and advantages of the invention will be seen as the following description of a particular embodiment progresses, in conjunction with the drawings, in which.

DESCRIPTION OF A PARTICULAR EMBODIMENT

Figure 1:
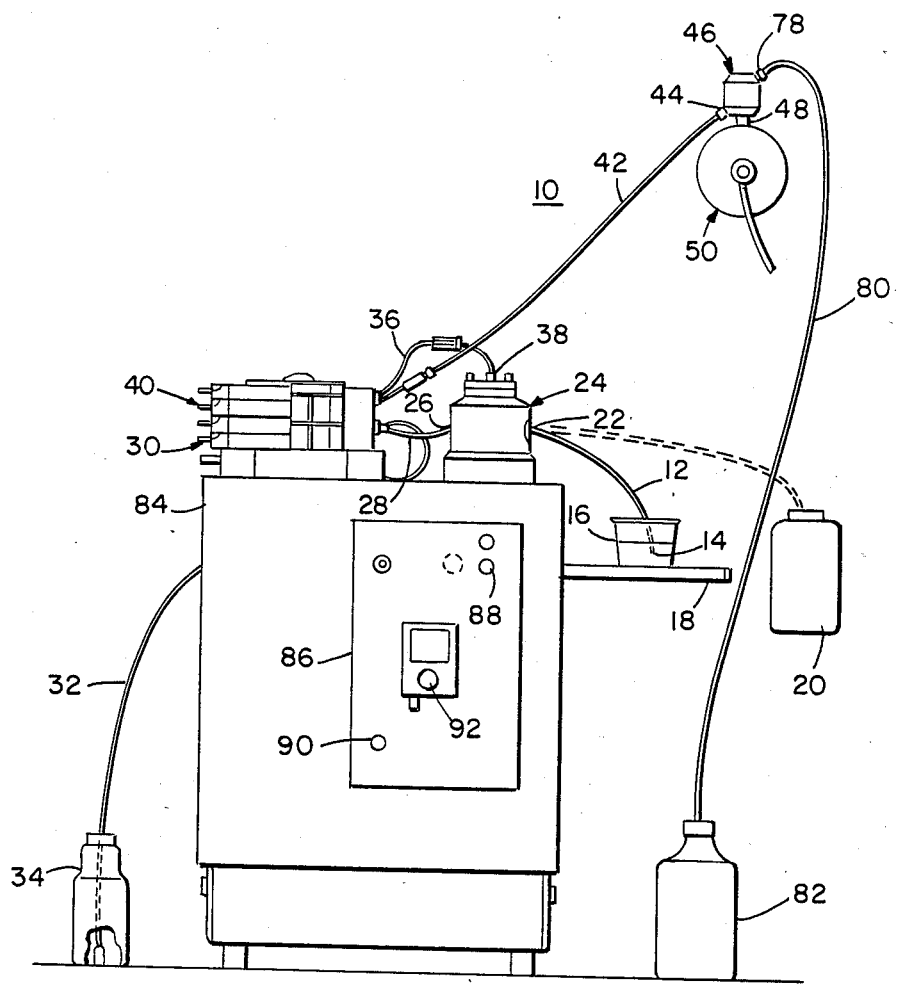
FIG. 1 is a front elevation view of a sample analysis system in accordance with the invention.
Figure 2:
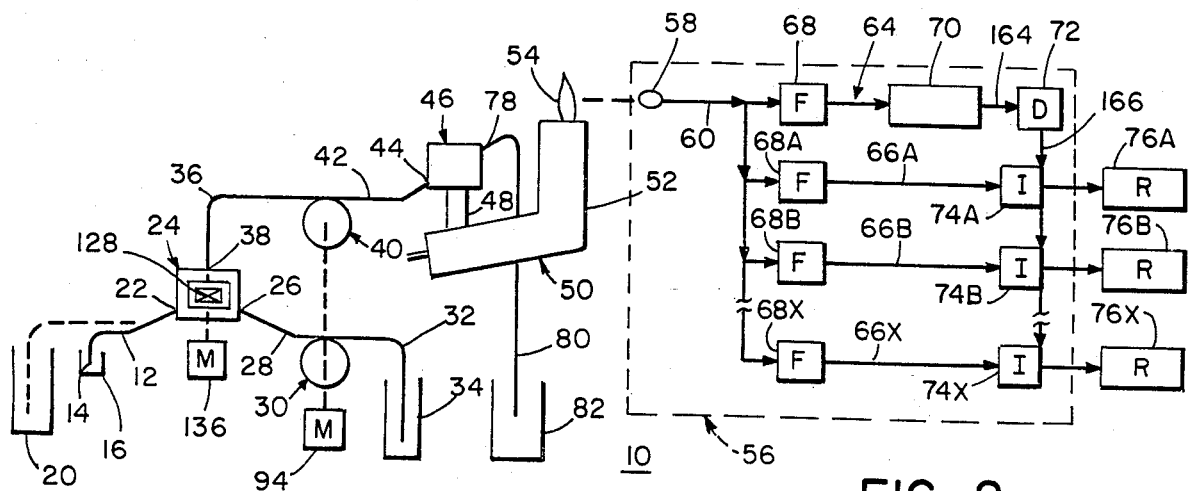
FIG. 2 is a diagrammatic view of the system shown in FIG. 1.

With reference to FIGS. 1 and 2, the analyzer system 10 includes inlet sample tube 12 that has an inlet end 14 movable between sample container 16 supported on sample tray 18 and cleaning liquid reservoir 20 that contains a suitable cleaning agent such as kerosene that includes tag material such as 10 ppm cobalt. It will be apparent that inlet line 12 may be connected to an appropriate data sampler in an automated system. Inlet tube 12 is connected to inlet 22 of mixing device 24. Connected to inlet 26 of mixing device 24 via line 28 and peristaltic pump section 30 and Viton tubing line 32 is diluent (kerosene) reservoir 34. Viton tubing line 36 is connected from outlet 38 of mixing device 24 to a second peristaltic pump 40 and line 42 extends from pump 40 to inlet 44 of debubbler unit 46. Branch 48 of debubbler unit is mounted on high solids nebulizer 50 that is coupled to induction coupled plasma torch 52 (FIG. 2). The output of torch 52 (diagrammatically indicated at 54) is monitored by spectroanalytical system 56 that includes radiation sensor 58. The output of sensor 58 is applied over line 60 to analyzer 56 for data interpretation and display of analytical results. Analyzer 56 includes control channel 64 and a plurality of data acquisition channels 66, each channel including a filter or other suitable wavelength selector 68. In a particular embodiment, control channel filter 68 is tuned to a suitable cobalt line such as 2286 Angstroms, a first data channel filter 68A is tuned to 2714 Angstroms (iron), a second data channel filter 68B is tuned to 2677 Angstroms (chromium), etc. Channel 64 also includes signal level sensing circuit 70 and delay circuit 72 while each data channel 66 includes integration circuitry 74 and data recording devices 76. This circuitry may be implemented in software and/or hardware form, as desired.

Connected to output 78 of debubbler 46 is line 80 that extends to drain 82.

As shown in FIG. 1, mixer 24 is mounted on housing 84 that includes a mixer control panel 86 with mixer motor control 88, pump motor control 90 and pump speed control 92.

The pump unit 30, 40 is manufactured by Rainin Instrument Co., Inc. of Woburn, Mass. and includes a variable speed drive 94 (FIG. 2) that enables pump cams to be driven at speeds of 1-25 RPM as controlled by controls 90, 92. Pumps 30 and 40 are simultaneously operated by drive motor 94 when the analyzer is in use, pump 40 pumping at a higher rate than pump 30 by use of pump tubes of different internal diameters, the pump tube with the larger internal diameter being associated with pump 40. By simply changing the size of one or both of the pump tubes, the respective rates of pumping can be conveniently adjusted as desired, for example to control dilution ratios—a typical dilution ratio being 10 to 1.

Figure 3:
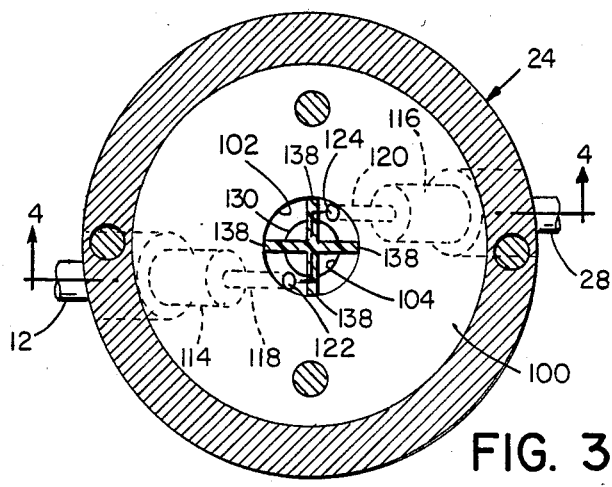
FIG. 3 is a sectional view through the mixing chamber of the system shown in FIG. 1.
Figure 4:
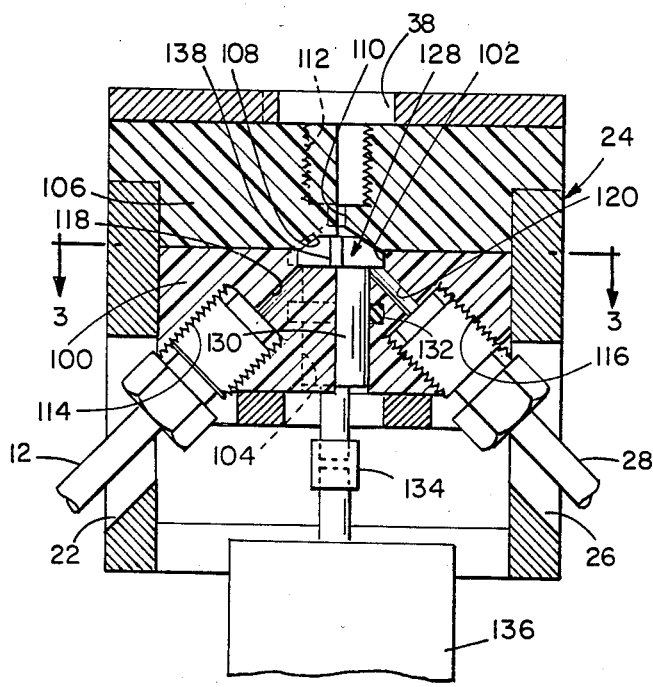
FIG. 4 is a sectional view taken along the line 4—4 of FIG. 3.

Further details of the mixing device 24 may be seen with reference to FIGS. 3 and 4. Mixing device 24 has Teflon body 100 in which cylindrical recess 102 and through passage 104 are formed. Teflon cover 106 was a conical surface 108 that mates with recess 102 and outlet passage 110 that extends to coupling 112. Also formed in body 100 are sample inlet coupling 114 and diluent inlet coupling 116, each of which communicates with passage 118, 120, respectively, that terminate in port 122, 124, respectively in the base of cylindrical cavity 102.

Disposed in mixing cavity 102 is Teflon mixing member 126 that includes impeller 128 and cylindrical body 130 that is received in passage 104 and sealed by seal 132 and connected via coupling 134 to drive motor 136.

Figure 5:
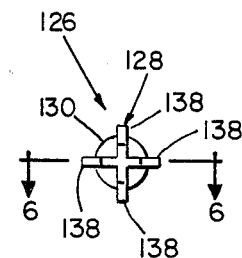
FIG. 5 is a top plan view of the impeller of the system shown in FIG. 1.
Figure 6:
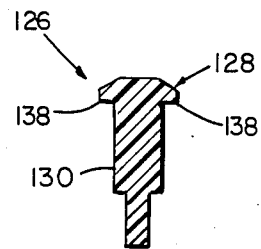
FIG. 6 is a sectional view taken along the line 6—6 of FIG. 5.

A top view of member 126 is shown in FIG. 5, and a sectional side view in FIG. 6. Impeller 128 has a diameter of about 0.9 centimeter and a height of about ¼ centimeter and impeller 128 includes four radially extending blades 138, each of which has a width of about one millimeter. Cylindrical body portion 130 has a length of about 1.2 centimeter and a diameter of about 0.6 centimeter. The dead volume in chamber 102 is about 0.1 milliliter.

Each impeller blade 138 has a frustroconical surface corresponding to the conical cover surface 108 and is inclined at an angle of about 60°. Motor 136 drives impeller 128 at a speed of 120 rpm.

Figure 7:
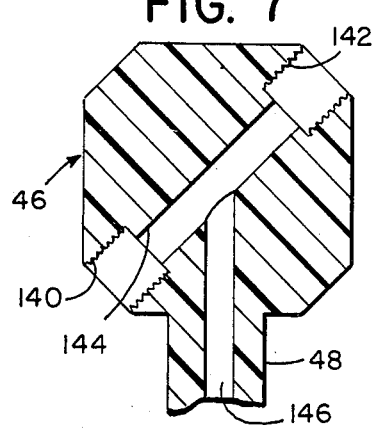
FIG. 7 is a sectional diagrammatic view of bubble separation apparatus employed in the system shown in FIG. 1.
Figure 8:
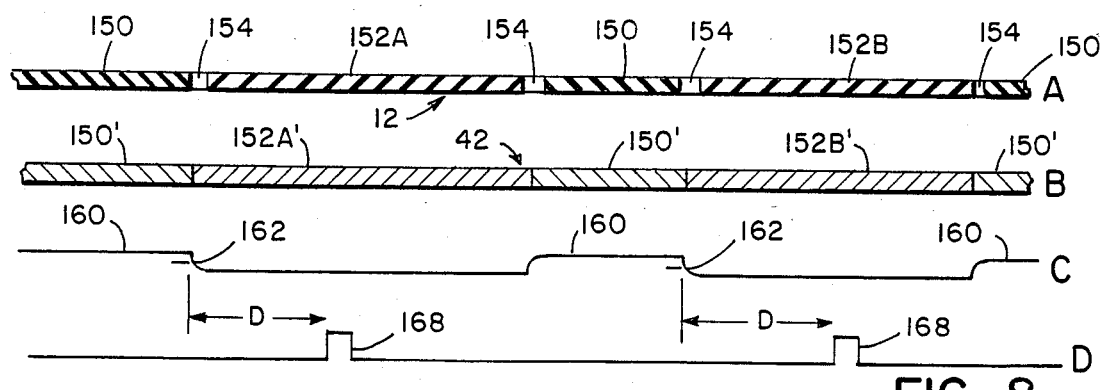
FIG. 8 is a series of diagrams indicating operation of the analyzer system shown in FIGS. 1 and 2.

Further details of the debubbler unit 46 may be seen with reference to FIG. 7. As diagrammatically indicated, unit 46 includes inlet socket 140 to which tube 42 is connected; drain socket 142 to which drain tube 80 is connected and support 48 that extends to nebulizer 50. Extending between sockets 140 and 142 is flow passage 144 that has a diameter of about one millimiter and is disposed at an upwardly inclined angle of about 45°. Sample passage 146 of slightly less than one millimeter and extends vertically downwardly through support 48 from inclined passage 144 to the input to nebulizer 50.

In standby, the inlet port 14 of sample tube 12 is submerged in the cleaning liquid in container 20 and when pump motor 94 is turned on (with control 90), pump 30 draws diluent from reservoir 34 into mixing chamber 102 and pump 40 draws the liquid from chamber 102 at a faster rate creating reduced pressure which is applied through line 12 to the cleaning liquid container 20 and cleaning liquid is aspirated into mixing chamber 102 for mixing with the diluent and flow of the mixture by pump 40 over line 42 through debubbler unit 46. Due to the mechanical mixing by the high speed rotation of impeller 128, there may be gas bubbles, for example, due to cavitation action of the impeller. With reference to FIG. 7, the mixture flows at a rate of about ten milliliters per minute through passage 144 with a minor friction (typically a few percent of the mixture) being flowed without gas bubbles through vertical passage 146 in response to nebulizer demand, the bubbles being flowed along the top of passage 144 over line 80 to drain 82. Dispersion of the diluted sample as an aerosol occurs in the nebulization chamber 50 and the resulting mixture in nebulized form is flowed to the ICP torch 52 where the sample is excited to spectroemissive levels for monitoring by the spectroanalyzer 56 whose outputs are applied to recorders 76.

When a sample is to be analyzed, the tip 14 of sample tube 12 is moved from the cleaning liquid container 20 to be submerged in a sample in container 16 on sample tray 18. As a series of samples are analyzed, sample tube tip 14 is left in a first sample for about twenty-five seconds and then transferred to the cleaning liquid for about five seconds, then submerged in the next sample for about twenty-five seconds, etc. As a result, there is a flow through input line 12 of a series of spaced quantities 150 of tagged cleaning liquid and quantities 152A, 152B of successive samples that are spaced from cleaning liquid quantities 150 by air bubbles 154 (FIG. 8A). After passing through mixer 24, pump 40 and debubbler 46, a bubble-free stream (FIG. 8B) flows through line 146 to nebulizer 50, the same general flow relation of samples 152 and cleaning liquid 150 being retained as diagrammatically indicated in FIG. 8B, quantities 152A′, 152B′ of successive diluted samples being spaced by quantities 150′ of diluted tagged cleaning liquid, each cleaning liquid quantity being of about five seconds time duration.

The analysis apparatus includes a tag monitoring channel 64 and discrete sample element monitoring channels 66. As indicated in FIG. 8C, each quantity of cleaning liquid being sensed causes cobalt channel circuit 68 to generate signal level 160. When circuit 70 senses that signal level 160 has decreased to half value, as indicated at 162, an output signal is applied over line 164 (FIG. 2) to delay 72 and twelve seconds later, a signal is applied over line 166 to initiate an integrating interval 168, each of the several sample channels 66 being activated for a two second integration interval as indicated at 168 in FIG. 8D and the resulting data values are applied to the corresponding recorder 76. Thus, the analysis sequence is controlled by detected sample materials and is independent of the particular timing or duration of sample introduction into tube 12. The system enables rapid, convenient and effective dilution and analysis of a variety of sample materials including viscous liquids such as heavy motor oils.

While a particular embodiment of the invention has been shown and described, various modifications thereof will be apparent to those skilled in the art, and therefore it is not intended that the invention be limited to the disclosed embodiment or to details thereof, and departures may be made therefrom within the spirit and scope of the invention.

What is claimed is:

1. A sample processing system for use with an analysis apparatus comprising structure defining a mixing chamber, mechanical mixing structure in said mixing chamber, means to drive said mechanical mixing structure, said mixing chamber having first and second inlets and an outlet, a sample conduit connected to said first inlet, a diluent conduit connected to said second inlet, a first positive displacement pump coupled to said diluent conduit for flowing diluent through said diluent conduit to said mixing chamber, a mixture conduit connected to said outlet, a second positive displacement pump coupled to said mixture conduit for flowing liquid from said mixing chamber through said mixture conduit, pump operating means adapted to drive said first and second positive displacement pumps concurrently for flowing liquid from said mixing chamber through said mixture conduit at a rate greater than the flow of diluent to said mixing chamber to create an aspiration force at said first inlet so as to aspirate a liquid through said first inlet into said mixing chamber for mixing with diluent and flow of the resulting diluted liquid from said mixing chamber through said mixture conduit, and bubble removal apparatus connected to said mixture conduit including a main flow passage and a branch passage extending downwardly from said main flow passage, said branch passage being adapted to be connected to flow a minor portion of the diluted liquid in said main flow passage in substantially bubble-free condition to analysis apparatus.

2. The system of claim 1 wherein the flow volume of liquid through said branch passage is less than ten percent of the flow volume of liquid through said main flow passage.

3. The system of claim 2 wherein said main flow passage of said bubble removal apparatus is upwardly inclined.

4. The system of claim 3 wherein said main flow passage and said branch passage each has a cross-sectional dimension of less than one-half centimeter.

5. The system of claim 1 wherein said mixing chamber has a volume of less than one milliliter and said mechanical mixing structure includes a bladed impeller.

6. The system of claim 5 wherein said said mechanical mixing structure drive means is adapted to drive said impeller in rotation at a speed of over 100 RPM.

7. The system of claim 1 and further including
a supply of cleaning liquid that includes tag material,
means for providing quantities of sample and cleaning liquids alternately to said mixing chamber,
analysis apparatus that includes sample sensing apparatus, a control channel and a plurality of data acquisition channels, all of said channels being responsive to the output of said sample sensing apparatus,
said control channel including tag material sensor means, and
means responsive to a predetermined change in the sensed tag material for activating said plurality of data acquisition channels.

8. The system of claim 7 wherein said tag material sensor means includes wavelength selector means tuned to a specific wavelength characteristic of said tag material, and said sensed tag material responsive means is adapted to activate said plurality of data acquisition channels in response to a predetermined change in the sensed magnitude of said specific wavelength characteristic of said sensed tag material.

9. The system of claim 8 wherein said cleaning liquid is hydrocarbon-based.

10. The system of claim 1 wherein the effective flow area of said mixture conduit is greater than the effective flow area of said diluent conduit.

11. The system of claim 10 wherein said mixing chamber has a volume of less than one milliliter, said mechanical mixing structure includes a bladed impeller, and said mechanical mixing structure drive means is adapted to drive said impeller in rotation at a speed of over 100 RPM.

12. The system of claim 11 wherein said main flow passage of said bubble removal apparatus is upwardly inclined, said branch passage extends generally vertically downwardly from said main flow passage, said main flow passage and said branch passage each has a cross-sectional dimension of less than one-half centimeter, and said liquid flowing means flowing liquid from said mixing chamber through said mixture conduit at a rate greater than the flow rate of liquid through said branch passage to said analysis apparatus, the flow rate of liquid through said branch passage being controlled by said analysis apparatus.

13. The system of claim 12 and further including
a supply of cleaning liquid that includes tag material,
means for providing quantities of sample and cleaning liquids alternately to said mixing chamber,
analysis apparatus that includes sample sensing apparatus, a control channel and a plurality of data acquisition channels, all of said channels being responsive to the output of said sample sensing apparatus,
said control channel including tag material sensor means, and
means responsive to a predetermined change in the sensed tag material for activating said plurality of data acquisition channels.

14. The system of claim 13 wherein said tag material sensor means includes wavelength selector means tuned to a specific wavelength characteristic of said tag material, and said sensed tag material responsive means is adapted to activate said plurality of data acquisition channels in response to a predetermined change in the sensed magnitude of said specific wavelength characteristic of said sensed tag material.

15. The system of claim 14 wherein said cleaning liquid is hydrocarbon-based and said tag material includes cobalt.

16. A spectrophotometer system comprising
induction coupled plasma apparatus for exciting sample material to spectroemissive levels,
nebulizer apparatus coupled to said induction coupled plasma apparatus for supplying a dispersion of sample material as an aerosol to said induction coupled plasma apparatus,
structure defining a mixing chamber,
said mixing chamber having first and second inlets and an outlet, a sample conduit connected to said first inlet, a diluent conduit connected to said second inlet, a first positive displacement pump coupled to said diluent conduit for flowing diluent through said diluent conduit to said mixing chamber, a mixture conduit connected to said outlet,
mechanical mixing structure in said mixing chamber,
means to drive said mechanical mixing structure to mix sample and diluent,
a second positive displacement pump coupled to said mixture conduit for flowing the resulting mixture from said mixing chamber through said mixture conduit, pump operating means adapted to drive said first and second positive displacement pumps concurrently for flowing liquid from said mixing chamber through said mixture conduit at a rate greater than the flow of diluent to said mixing chamber to create an aspiration force at said first inlet so as to aspirate a liquid through said first inlet into said mixing chamber for mixing with diluent and flow of the resulting diluted liquid from said mixing chamber through said mixture conduit, bubble removal apparatus connected to said mixture conduit including a main flow passage and a branch passage extending downwardly from said main flow passage to said nebulizer, said branch passage being adapted to be connected to flow a minor portion of the diluted sample mixture in said main flow passage in substantially bubble-free condition to said nebulizer and application of said diluted sample mixture as an aerosol dispersion to said induction coupled plasma analysis apparatus for excitation to spectroemissive levels, and analysis apparatus in optically coupled relation to said induction coupled plasma apparatus.

17. The system of claim 16 and further including a supply of cleaning liquid that includes tag material, and means for providing quantities of sample and cleaning liquids alternately to said mixing chamber, and wherein said analysis apparatus includes photosensor means responsive to the output of said induction coupled plasma apparatus, a control channel and a plurality of data acquisition channels, all of said channels being responsive to the output of said photosensor means, said control channel including tag material sensor means, and means responsive to a predetermined change in the sensed tag material for activating said plurality of data acquisition channels to record data on elements of the sample mixture excited by said induction coupled plasma apparatus.

18. The system of claim 19 wherein said tag material sensor means includes wavelength selector means tuned to a specific wavelength characteristic of said tag material excited to spectroemissive levels, and said sensed tag material responsive means is adapted to activate said plurality of data acquisition channels in response to a predetermined change in the sensed magnitude of said specific wavelength characteristic of said tag material as sensed by said tag material sensor means to acquire data on elements in said sample that are excited to spectroemissive levels by said induction coupled plasma apparatus.

19. The system of claim 18 wherein said cleaning liquid is hydrocarbon-based and said tag material includes cobalt.

20. The system of claim 18 wherein said mixing chamber has a volume of less than one milliliter, said mechanical mixing structure includes a bladed impeller, and said mechanical mixing structure drive means is adapted to drive said impeller in rotation at a speed of over 100 RPM.

21. The system of claim 20 wherein said main flow passage of said bubble removal apparatus is upwardly inclined, said branch passage extends generally vertically downwardly from said main flow passage, and said main flow passage and said branch passage each has a cross-sectional dimension of less than one-half centimeter, and the flow rate through said branch passage is controlled by said nebulizer.

22. A spectrophotometer system comprising induction coupled plasma apparatus for exciting sample material to spectroemissive levels, nebulizer apparatus coupled to said induction coupled plasma apparatus for supplying a dispersion of sample material as an aerosol to said induction coupled plasma apparatus, structure defining a mixing chamber, means for providing quantities of sample liquids to be analyzed and cleaning liquid that contains tag material alternately to said nebulizer apparatus for application as an aerosol dispersion to said induction coupled plasma analysis apparatus for excitation to spectroemissive levels, and analysis apparatus in optically coupled relation to said induction coupled plasma apparatus, said analysis apparatus including a control channel and a plurality of data acquisition channels, all of said channels being responsive to the output of said induction coupled plasma apparatus, said control channel including tag material sensor means, and means responsive to a predetermined change in the sensed tag material for activating said plurality of data acquisition channels to record data on elements of sample liquids excited by said induction coupled plasma apparatus.

23. The system of claim 22 wherein said tag material sensor means includes wavelength selector means tuned to a specific wavelength characteristic of said tag material excited to spectroemissive levels, and said sensed tag material responsive means is adapted to activate said plurality of data acquisition channels in response to a predetermined change in the magnitude of said specific wavelength characteristic of said tag material as sensed by said tag material sensor means to acquire data on elements in sample liquids that are excited to spectroemissive levels by said induction coupled plasma apparatus.

24. The system of claim 23 wherein said cleaning liquid is hydrocarbon-based.

25. The system of claim 22 and further including structure defining a mixing chamber, said mixing chamber having first and second inlets and an outlet, means for supplying said sample liquid to be analyzed to said first inlet, means for supplying diluent to said second inlet, a mixture conduit connected to said outlet, mechanical mixing structure in said mixing chamber, means to drive said mechanical mixing structure to mix sample and diluent, means for flowing the resulting mixture from said mixing chamber through said mixture conduit, and bubble removal apparatus connected to said mixture conduit including a main flow passage and a branch passage extending downwardly from said main flow passage to said nebulizer, said branch passage adapted to be connected to flow a minor portion of the diluted sample mixture in said main flow passage in substantially bubble-free condition to said nebulizer at a flow rate controlled by said nebulizer.

26. The system of claim 25 and further including a sample conduit connected to said first inlet, a diluent conduit connected to said second inlet, first positive displacement pump coupled to said diluent conduit for flowing diluent through said diluent conduit to said mixing chamber, and wherein said mixture flowing means includes a second positive displacement pump coupled to said mixture conduit, and pump operating means adapted to drive said first and second positive displacement pumps concurrently for flowing liquid from said mixing chamber through said mixture conduit at a rate greater than the flow of diluent to said mixing chamber to create as aspiration force at said first inlet so as to aspirate a liquid through said first inlet into said mixing chamber for mixing with diluent and flow of the resulting diluted liquid from said mixing chamber through said mixture conduit.

27. The system of claim 26 wherein said mixing chamber has a volume of less than one milliliter, said mechanical mixing structure includes a bladed impeller, and said mechanical mixing structure drive means is adapted to drive said impeller in rotation at a speed of over 100 RPM.

28. The system of claim 27 wherein said main flow passage of said bubble removal apparatus is upwardly inclined, said branch passage extends generally vertically downwardly from said main flow passage, and said main flow passage and said branch passage each has a cross-sectional dimension of less than one-half centimeter.

* * * * *

UNITED STATES PATENT AND TRADEMARK OFFICE
CERTIFICATE OF CORRECTION

PATENT NO. : 4,804,519

DATED : February 14, 1989

INVENTOR(S) : Mario A. Sainz, et al.

It is certified that error appears in the above-identified patent and that said Letters Patent is hereby corrected as shown below:

Col. 4, line 7, "friction" should be --fraction--.

Col. 4, line 38, after "tag" --[cobalt]-- should be inserted.

Col. 7, claim 18, line 44, "19" should be --17--.

Signed and Sealed this

Sixth Day of February, 1990

Attest:

JEFFREY M. SAMUELS

Attesting Officer     Acting Commissioner of Patents and Trademarks